(12) United States Patent
Schiffer (10) Patent No.: US 12,297,041 B1
(45) Date of Patent: May 13, 2025

(54) SMART DIAPER PAIL

(71) Applicant: Verily Life Sciences LLC, South San Francisco, CA (US)

(72) Inventor: Brian Schiffer, San Francisco, CA (US)

(73) Assignee: Verily Life Sciences LLC, Dallas, TX (US)

( * ) Notice: Subject to any disclaimer, the term of this patent is extended or adjusted under 35 U.S.C. 154(b) by 1137 days.

(21) Appl. No.: 16/948,446

(22) Filed: Sep. 18, 2020

Related U.S. Application Data (60) Provisional application No. 62/902,995, filed on Sep. 20, 2019.

(51) Int. Cl.
*B65F 1/16* (2006.01)
*B65F 1/14* (2006.01)
(Continued)

(52) U.S. Cl.
CPC ............... *B65F 1/16* (2013.01); *B65F 1/14* (2013.01); *G01G 19/52* (2013.01); *G01G 19/62* (2013.01); *G01N 21/6486* (2013.01); *G08B 13/14* (2013.01); *B65F 2001/1676* (2013.01); *B65F 2210/128* (2013.01); *B65F 2210/139* (2013.01);
(Continued)

(58) Field of Classification Search
CPC ...... G08B 21/18; G08B 21/182; G08B 21/20; G08B 21/24; G08B 21/245; G08B 13/14; B65F 1/16; B65F 1/14; B65F 2001/1676; B65F 2210/128; B65F 2210/139; B65F 2210/168; B65F 2210/184; B65F 2240/132; G01G 19/52; G01G 19/62; G01N 21/6486; G01N 2201/1244

USPC ...... 340/573.5, 603–605, 613; 604/358, 361, 604/403, 404; 206/438
See application file for complete search history.

(56) References Cited

U.S. PATENT DOCUMENTS 4,315,159 A  2/1982  Niwa et al.
4,336,459 A  6/1982  Fay
(Continued)

FOREIGN PATENT DOCUMENTS

CN   106999118 A   8/2017
CN   107095744 A   8/2017
(Continued)

OTHER PUBLICATIONS

European Application No. 20855207.5, "Extended European Search Report", Sep. 26, 2022, 7 pages.
(Continued)

*Primary Examiner* — Brian Wilson
(74) *Attorney, Agent, or Firm* — Kilpatrick Townsend & Stockton LLP (57) ABSTRACT

A diaper pail is disclosed. The diaper pail includes a scale configured to determine a weight of an absorbent article. The diaper pail further includes a light source positioned to transmit light at an excitation wavelength of a biological substance. The diaper pail further includes a photodetector positioned to detect a measurement of light intensity within the range of emission wavelengths of the biological substance. The diaper pail includes a processor that is configured to execute processor-executable instructions to receive the weight of the absorbent article and the measurement of light intensity and to detect a presence of the biological substance on the absorbent article.

13 Claims, 7 Drawing Sheets

(51) Int. Cl.
*G01G 19/52* (2006.01)
*G01G 19/62* (2006.01)
*G01N 21/64* (2006.01)
*G08B 13/14* (2006.01)

(52) U.S. Cl.
CPC ... *B65F 2210/168* (2013.01); *B65F 2210/184* (2013.01); *B65F 2240/132* (2013.01); *G01N 2201/1244* (2013.01)

(56) References Cited

U.S. PATENT DOCUMENTS

| | | | |
|---|---|---|---|
| 5,520,303 | A | 5/1996 | Bernstein et al. |
| 5,751,418 | A | 5/1998 | Kimura et al. |
| 5,821,546 | A | 10/1998 | Xiao et al. |
| 5,895,920 | A | 4/1999 | Carlsson |
| 6,094,274 | A | 7/2000 | Yokoi |
| 6,603,126 | B2 | 8/2003 | Yamada et al. |
| 9,820,891 | B2 | 11/2017 | Abir |
| 11,850,118 | B2 | 12/2023 | Schiffer |
| 2003/0230728 | A1 | 12/2003 | Dai et al. |
| 2008/0265177 | A1 | 10/2008 | Connally et al. |
| 2010/0168694 | A1 | 7/2010 | Gakhar et al. |
| 2011/0117025 | A1 | 5/2011 | Dacosta et al. |
| 2011/0178411 | A1 | 7/2011 | Roth et al. |
| 2012/0116337 | A1 | 5/2012 | Ales et al. |
| 2014/0379588 | A1* | 12/2014 | Gates ............... G06T 7/0008 705/308 |
| 2015/0148630 | A1 | 5/2015 | Meester |
| 2017/0252225 | A1 | 9/2017 | Arizti et al. |
| 2017/0348162 | A1* | 12/2017 | Arizti ................. A61F 13/58 |
| 2018/0016096 | A1* | 1/2018 | Krishnamurthy ........ B65F 1/14 |
| 2018/0024060 | A1 | 1/2018 | Rochette et al. |
| 2018/0149635 | A1* | 5/2018 | Abir ................. A61F 13/42 |
| 2018/0185206 | A1 | 7/2018 | Kuniavsky et al. |
| 2018/0292381 | A1* | 10/2018 | Faybishenko ........ B65F 1/1623 |
| 2021/0045934 | A1 | 2/2021 | Schiffer |
| 2022/0252515 | A1* | 8/2022 | Vojnovic ............ G01N 21/6408 |

FOREIGN PATENT DOCUMENTS

| | | |
|---|---|---|
| EP | 3213727 A1 | 9/2017 |
| KR | 20140084060 A | 7/2014 |

OTHER PUBLICATIONS

"Getting the Best Out of Photodiode Detectors", Advanced Technology Development Group, Gray Cancer Institute, 2005, 7 pages.
Ashby et al., "Fluorescence of Dietary Porphyrins as a Basis for Real-Time Detection of Fecal Contamination on Meat", Journal of Agriculture and Food Chemistry, vol. 51, No. 11, May 21, 2003, pp. 3502-3507.
Brown, "Advanced Planar Light Guide Solar Concentrators", The Institute of Optics, 2013, 199 pages.
Chen et al., "Spectral Characteristics of Autofluorescence and Second Harmonic Generation from Ex Vivo Human Skin Induced by Femtosecond Laser and Visible Lasers", Scanning, vol. 28, No. 6, Nov.-Dec. 2006, pp. 319-326.
Chisolm et al., "Quantitative Urinary Coproporphyrin Excretion and its Relation to Edathamil Calcium Disodium Administration in Children with Acute Lead Intoxication", J. Clin. Invest., vol. 35, No. 10, Oct. 1956, pp. 1131-1138.
Cho et al., "Potential Application of Fluorescence Imaging for Assessing Fecal Contamination of Soil and Compost Maturity", Applied Sciences, vol. 6, No. 9, Aug. 2016, 12 pages.
Croizat et al., "Understanding the Delayed Fluorescence of Protoporphyrin IX to Quantify pO2 in Biological Tissues", Swiss Biomedical Photonics Network Annual Meeting, Dec. 2017, 2 pages.
Drobizhev et al., "Photon Energy Upconversion in Porphyrins: One-Photon Hot-Band Absorption Versus Two-Photon Absorption", Chemical Physics Letters, vol. 370, Nos. 5-6, Mar. 21, 2003, pp. 690-699.

Haining et al., "Rapid Porphyrin Screening of Urine, Stool, and Blood", Clin. Chem., vol. 15, No. 6, Jun. 1969, pp. 460-466.
Hall, "Navigating the Lab-on-Chip Manufacturability Roadblock: Scalable, Low-Cost Fluorescence Detection for Lab-on-Chip Instrumentation with Rapid-Prototyped Microfluidics", Electrical and Computer Engineering Theses, Apr. 30, 2018, 291 pages.
IEP, "Low-Noise Preamplifier for Capacitive Sensors", Department of Electrical Engineering and Computer Science, Jun. 1995, 129 pages.
Jacob et al., "Excretion Pattern of Faecal Coproporphyrin Isomers I-IV in Human Porphyrias", Eur. J. Clin. Chem. Clin. Biochem., vol. 33, No. 12, Dec. 1995, pp. 893-901.
Jope et al., "Spectral Absorption and Fluorescence of Coproporphyrin Isomers I and III and the Melting-Points of Their Methyl Esters", Biochemical Journal, vol. 39, No. 3, Jan. 1, 1945, pp. 239-244.
Kantere et al., "Anti-Stokes Fluorescence from Endogenously Formed Protoporphyrin IX—Implications for Clinical Multiphoton Diagnostics", Journal of Biophotonics, vol. 6, No. 5, May 2013, pp. 409-415.
Leahy et al., "A Simple Method for the Separation and Quantification of Urinary Porphyrins", J. Clin. Pathol., vol. 35, No. 11, Nov. 1982, pp. 1232-1235.
Lefcourt et al., "A Transportable Fluorescence Imagining System for Detecting Fecal Contaminants", Computers and Electronics in Agriculture, vol. 48, No. 1, Jul. 2005, pp. 63-74.
Localio et al., "The Urinary/Fecal Coproporphyrin Ratio in Liver Disease", J. Clin. Invest., vol. 20, vol. 1, Jan. 1941, pp. 7-11.
Lowndes, "Blood Interference in Fluorescence Spectrum—Experiment, Analysis and Comparison with Intraoperative Measurements on Brain Tumor", Institute of Technology, Linkoping University, Jul. 9, 2010, 42 pages.
Markwardt et al., "405 nm Versus 633 nm for Protoporphyrin IX Excitation in Fluorescence-Guided Stereotactic Biopsy of Brain Tumors", Journal of Biophotonics, vol. 9, No. 9, Sep. 2016, pp. 901-912.
Mik et al., "Mitochondrial PO2 Measured by Delayed Fluorescence of Endogenous Protoporphyrin IX", Nature Methods, vol. 3, No. 11, Dec. 2006, 159 pages.
Minder et al., "Age-Dependent Reference Values of Urinary Porphyrins in Children", Eur. J. Clin. Chem. Clin. Biochem., vol. 34, No. 5, May 1996, pp. 439-443.
Moore et al., "Disorders of Porphyrin Metabolism", Springer Science & Business Media, 1998, 382 pages.
Oh et al., "Detection of Fecal Contamination on Beef Meat Surfaces Using Handheld Fluorescence Imaging Device (HFID)", Sensing for Agriculture and Food Quality and Safety VIII, Proceedings of SPIE, vol. 9864, May 17, 2016, pp. 986411-1-986411-6.
Roberts et al., "Red-Light Excitation of Protoporphyrin IX Fluorescence for Subsurface Tumor Detection", J. Neurosurg., vol. 128, No. 6, Jun. 2018, pp. 1690-1697.
Rocchi et al., "Coproporphyrin Excretion in Healthy Newborn Babies", Journal of Pediatric Gastroenterology and Nutrition, vol. 3, No. 3, Jun. 1984, pp. 402-407.
Tewari et al., "Quantitative Estimation of Coproporphyrin III and Protoporphyrin IX from Their Mixture by Spectrofluorometry", Journal of Plant Biochemistry and Biotechnology, vol. 7, No. 1, Jan. 1998, pp. 43-46.
Tian, "Anti-Stokes Fluorescence Spectroscopy and Imaging for Cutaneous Porphyrin Detection", A Thesis Submitted in Partial Fulfillment of the Requirements for the Degree of Master of Science in the Faculty of Graduate and Posdoctoral Studies (Physics), The University of British Columbia, Feb. 2015, 89 pages.
Troy et al., "Quantitative Comparison of the Sensitivity of Detection of Fluorescent and Bioluminescent Reporters in Animal Models", Molecular Imaging, vol. 3, No. 1, Jan. 2004, pp. 9-23.
Tung et al., "PDMS-Based Opto-Fluidic Micro Flow Cytometer with Two-Color, Multi-Angle Fluorescence Detection Capability Using PIN Photodiodes", Sensors and Actuators B Chemical, vol. 98, No. 2, Mar. 2004, pp. 356-367.
Vargas, "Detection of Fecal Contamination on Cantaloupes and Strawberries Using Hyperspectral Fluorescence Imagery", Thesis submitted to the Faculty of the Graduate School of the University (56) References Cited

OTHER PUBLICATIONS of Maryland, College Park, in Partial Fulfillment of the Requirements for the Degree of Master of Science, May 8, 2006, 82 pages.
Yamamoto et al., "Local Temperature Variation Measurement by Anti-Stokes Luminescence in Attenuated Total Reflection Geometry", Optics Express, vol. 24, No. 17, Aug. 22, 2016, pp. 19026-19031.
U.S. Appl. No. 16/542,898, Non-Final Office Action, Mailed on Jan. 6, 2022, 9 pages.
U.S. Appl. No. 16/542,898, Notice of Allowance, Mailed on Mar. 22, 2022, 10 pages.
U.S. Appl. No. 17/843,186, "Non-Final Office Action", Mar. 17, 2023, 16 pages.
CN202080057932.3, "Office Action", Mar. 15, 2023, 8 pages.
U.S. Appl. No. 17/843,186, Notice of Allowance, Aug. 3, 2023, 10 pages.
CN Appl. No. 202080057932.3, Notice of Decision to Grant, Oct. 13, 2023, 4 pages.
International Application No. PCT/US2020/042022, International Search Report and Written Opinion mailed on Oct. 15, 2020, 7 pages.
Europe Appl. No. 20855207.5, Office Action, Dec. 3, 2024, 8 pages.

\* cited by examiner

SMART DIAPER PAIL

CROSS-REFERENCE TO RELATED APPLICATIONS

This application claims priority to U.S. Provisional Patent Application No. 62/902,995, filed Sep. 20, 2019, titled "Smart Diaper Pail," the entirety of which is hereby incorporated by reference.

FIELD

The present application relates to a diaper pail that analyzes the contents and weight of an absorbent article, and in particular, to a diaper pail that can stimulate and measure auto-fluorescence in a diaper to determine a presence of a biological substance in the absorbent article.

SUMMARY

Techniques described herein relate to diaper pails. In an example, a diaper pail includes a scale configured to determine a weight of an absorbent article. The diaper pail further includes a light source positioned to transmit light directed at one or more sides of the absorbent article on the scale. The light includes a peak excitation wavelength that corresponds to an excitation wavelength of a biological substance such that the light is configured to trigger the biological substance to emit light within a range of emission wavelengths. The diaper pail further includes a photodetector configured to detect light intensity within the range of emission wavelengths of the biological substance and to output a measurement of the light intensity. The photodetector is positioned to detect light emitted from one or more of the sides of the absorbent article. The diaper pail further includes a processor configured to execute processor-executable instructions which cause the processor to receive, from the scale, the weight of the absorbent article, receive, from the photodetector, the measurement of the light intensity. The processor-executable instructions further cause the processor to compare the measurement of light intensity to a light intensity threshold or determine that the weight of the absorbent article is greater than a weight threshold. The processor-executable instructions further cause the processor to determine a presence of the biological substance on the absorbent article based on the comparing or determining. The processor-executable instructions further cause the processor to transmit a message indicating the presence of the biological substance to an external device.

BACKGROUND

Some existing solutions exist for determining a presence or level of bodily exudate in an absorbent article such as a diaper. But often, such solutions require a level of user interaction that may be difficult or cumbersome, such as wearing a sensor. Hence, new solutions are needed.

BRIEF DESCRIPTION OF THE DRAWINGS

Features, embodiments, and advantages of the present disclosure are better understood when the following Detailed Description is read with reference to the accompanying drawings.

DETAILED DESCRIPTION

Aspects described herein provide solutions for tracking the health of a wearer of an absorbent article, such as a diaper, without requiring that a wearer of the diaper wear any kind of sensor. In an aspect, a smart diaper pail receives a soiled diaper and detects a presence or an amount of bodily exudate (e.g., urine or feces) in the diaper. The smart diaper pail can include multiple chambers including a weighing chamber, in which a diaper can be weighed, and an analysis chamber, where a diaper can be analyzed by stimulated auto-fluorescence or Volatile Organic Compound (VOC) sensors, and a waste chamber in which any soiled diapers can be stored after weighing and analysis. The analysis can be used to create logs of bodily exudate over time (e.g., as determined by analyzing subsequent soiled diapers), or to determine trends or irregularities, for example, how often an infant soils its diaper, or whether the infant is sufficiently hydrated.

In an example, a user places a soiled diaper in the diaper pail. The diaper can be in an open position (e.g., simply placed in the pail) or a closed position (e.g., bundled into a ball with the sticky tabs of the diaper). The diaper lands in a weighing chamber, where the diaper is weighed. Upon completion of weighing, a door between the weighing chamber and the analysis chamber automatically opens, causing the diaper to fall into the analysis chamber. The analysis chamber includes devices that can stimulate auto-fluorescence (e.g., as light sources) and detection devices (e.g., photodetectors, or VOC sensors). The devices in the analysis chamber, in conjunction with a computing device that is in the smart diaper pail or is located externally, determine a presence or absence of either urine or fecal matter. Upon the completion of the analysis, an additional door below the analysis chamber opens into a waste chamber, where the diaper can be sealed into a bag or otherwise sealed to prevent odors escaping the diaper pail. In another aspect, the diaper pail includes a weighing chamber that is integrated with the waste chamber. In this aspect, the diaper is initially placed in the analysis chamber, then a door can cause the diaper to fall into the weighing chamber, where weighing takes place.

Certain aspects stimulate and detect auto-fluorescence of biological substances such as substances contained within urine or feces. Auto-fluorescence refers to a natural emission of light of certain substances in response to absorbing light (e.g., being stimulated with a light source). A molecule that exhibits fluorescence is called a fluorophore. Detectable substances include biological structures such as chlorophyll, bilirubin, and porphyrin. For example, the smart diaper pail causes an internal light source to emit light on a diaper when the diaper is within an analysis chamber. When the light source reaches any fecal matter, the light excites one or more biological structures within the fecal matter, causing light to be emitted by auto-fluorescence. The emitted light is measured by one or more detectors. The wavelength(s) of the emitted light and/or the light that is detected can be adjusted to maximize fluorescence of the particular biological substance(s) to be detected and to minimize an effect of other objects or substances fluorescing. This application relates to U.S. patent application Ser. No. 16/542,898, entitled "Determining a presence of auto-fluorescent biological substances through an article," which is incorporated herein by reference.

Disclosed solutions can adjust the wavelength(s) of emitted light to maximize a response of the substance to be detected and to minimize fluorescence of the article or any other substances. For example, an excitation wavelength with a lower absorption can sometimes result in a lower total intensity of emission, but there is not necessarily a direct linear correlation. This property can be leveraged to minimize background fluorescence by choosing an excitation spectra that includes peaks representing wavelengths that are poorly absorbed by any background material, including any undesired fluorophores, and high for the substance of interest. Alternatively, a ratio-based approach of sensing can be done by using multiple excitation wavelengths and measuring the difference in response.

In an example, light with one or more peak wavelengths is provided to an article. In turn, light emitted at one or more ranges of emission wavelengths can be detected. For example, disclosed solutions can excite a substance by providing light that includes two different peak wavelengths, each of which corresponds to an excitation wavelength of a biological substance that is to be detected. In an example, light with a first peak emission wavelength is first emitted, followed by a first measurement of the response, then light that includes a second peak emission wavelength is emitted, followed by a second measurement of a subsequent response. By analyzing an intensity of the measurements and/or a ratio of the measurements, disclosed solutions can detect a presence of a biological substance. Any number of excitation wavelengths and/or emission wavelengths can be used. The peak wavelengths can be identical or different. The peak wavelengths can overlap or not overlap, e.g., be mutually exclusive. Different combinations are possible.

Figure 1:
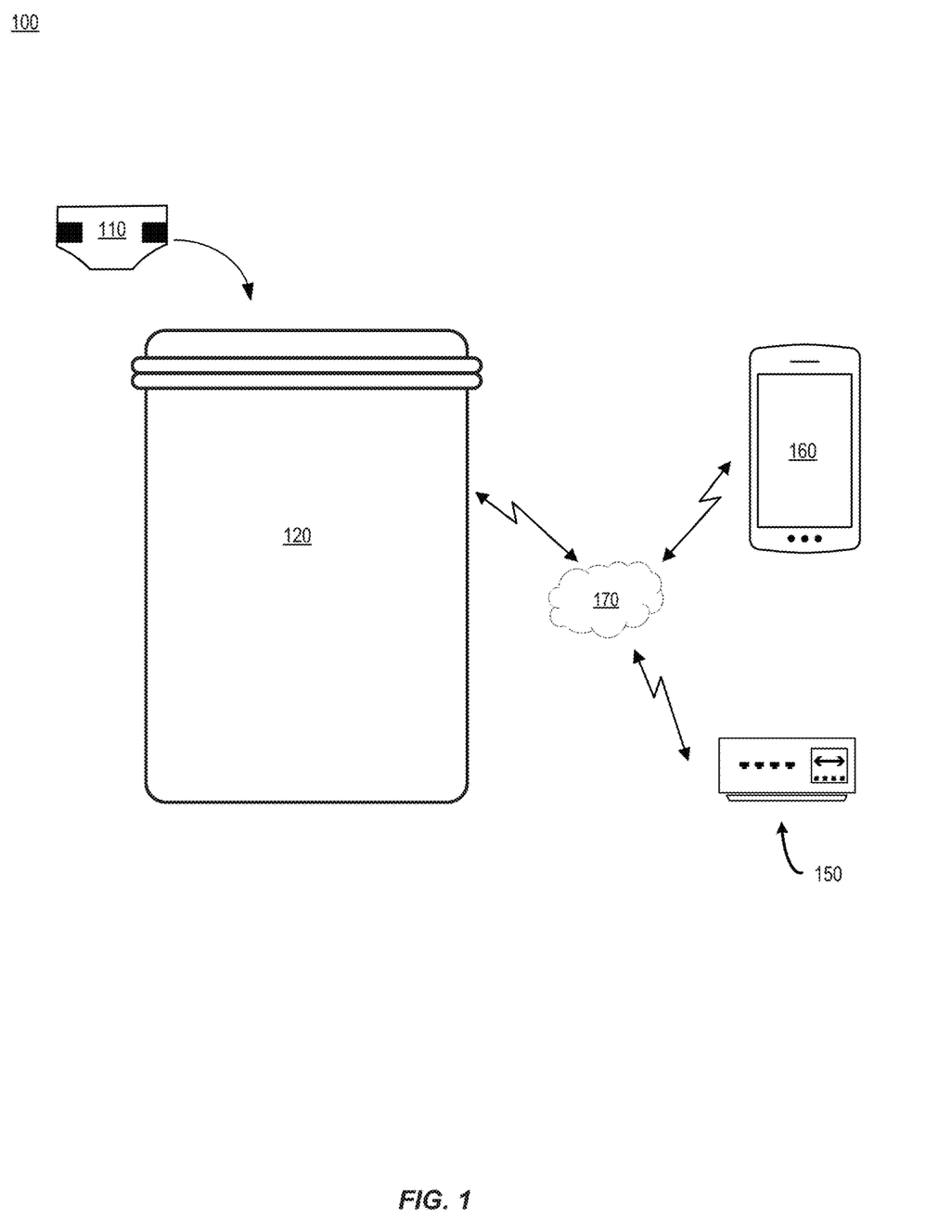
FIG. 1 is a block diagram of an example of a smart diaper pail, according to certain aspects of the present disclosure.

Turning now to the figures, FIG. 1 is a block diagram of an example of a smart diaper pail, according to certain aspects of the present disclosure. FIG. 1 includes smart diaper pail environment 100, which includes one or more of article 110, smart diaper pail 120, hub 150, mobile device 160, and network 170.

As depicted in FIG. 1, smart diaper pail 120 can receive article 110, weigh article 110, and/or analyze article 110 to determine a presence of, absence of, or amount of bodily exudate in article 110. Article 110 can be any suitable absorbent article such as a disposable diaper, a reusable cloth diaper, pantiliner, adult diaper, etc. Smart diaper pail 120 can store article 110 for later disposal while maintaining an odor-free environment outside smart diaper pail 120.

Figure 2:
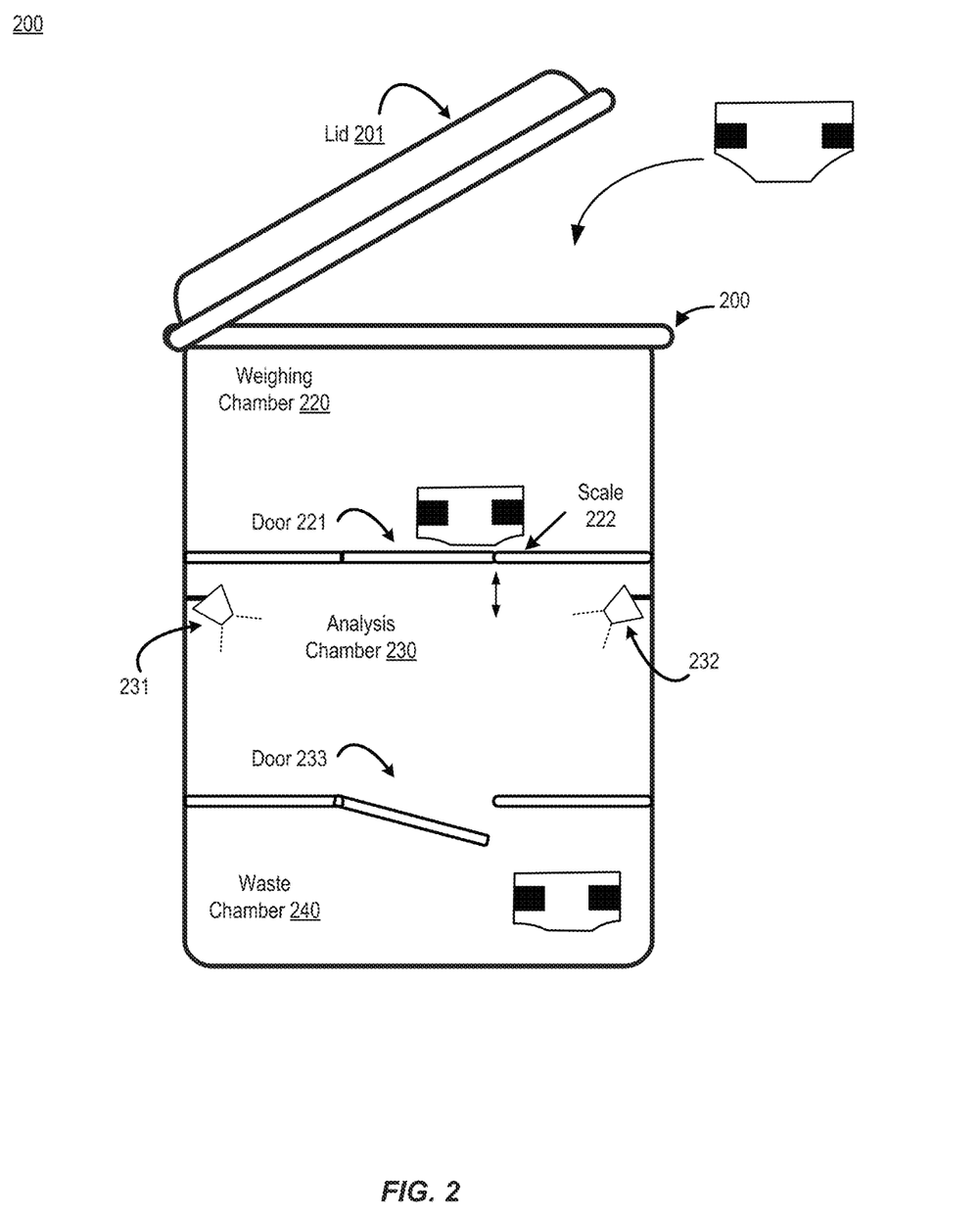
FIG. 2 is a side view of a first example of a smart diaper pail, according to certain aspects of the present disclosure.
Figure 3:
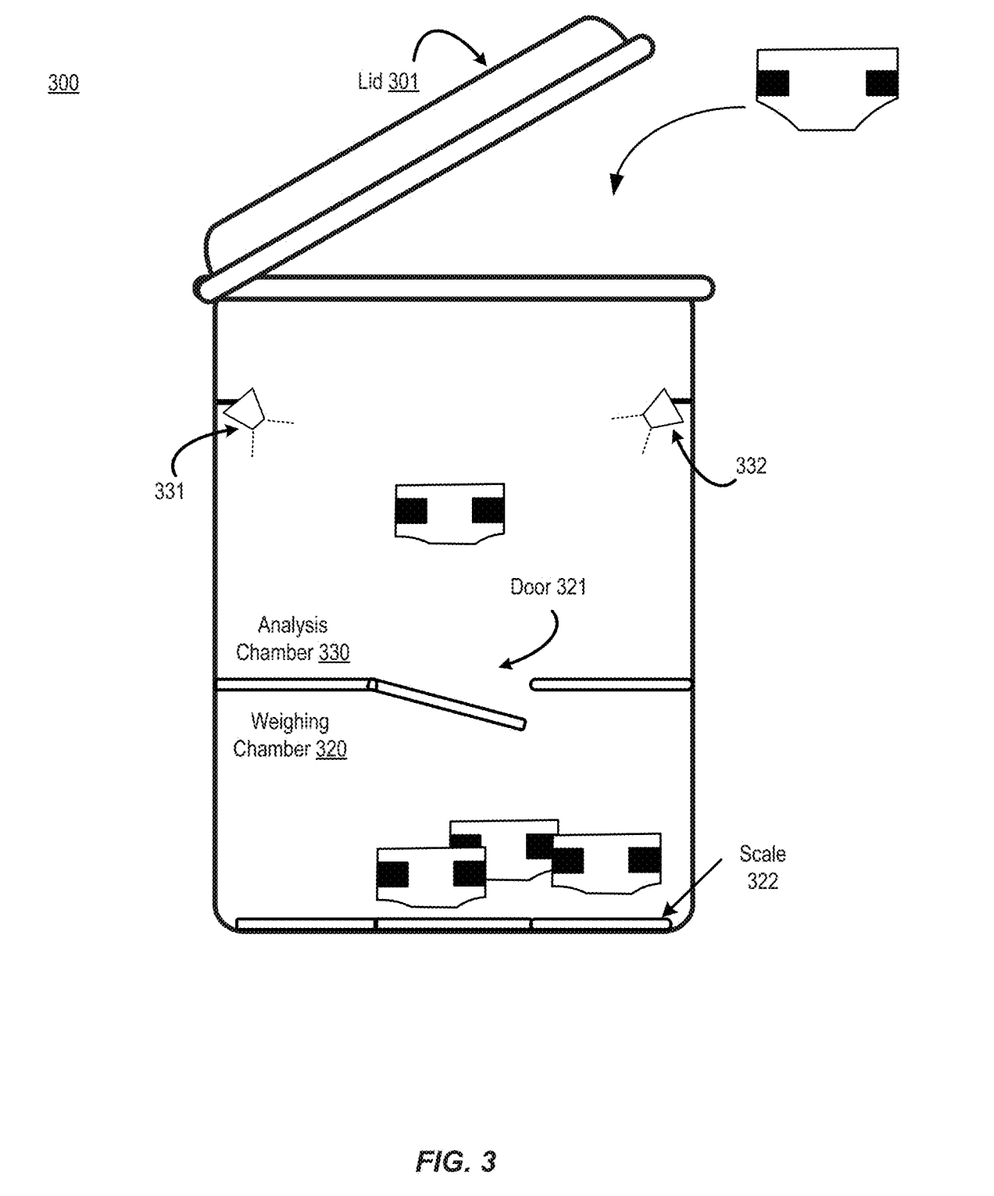
FIG. 3 is a side view of a first example of a smart diaper pail, according to certain aspects of the present disclosure.

Smart diaper pail 120 can communicate the weight, presence, or amount to hub 150 and/or mobile device 160. Smart diaper pail 120, hub 150, and mobile device 160 can be connected by network 170. Network 170 can be any wired, or wireless network such as Ethernet, WiFi, Bluetooth, etc. Smart diaper pail 120 can be powered by either mains power or battery power. In some cases, powering the smart diaper pail 120 by mains power can enable the smart diaper pail 120 to perform more sophisticated and power-consuming analysis such as a longer and more light-intensive auto-fluorescence stimulation. Smart diaper pail 120 can include different chambers, such as a weighing chamber, analysis chamber, or waste chamber. FIGS. 2 and 3 depict examples of different configurations of smart diaper pails. Other configurations are possible.

Hub 150 can include a transmitter or transceiver capable of transmitting a radio signal to an external device. Hub 150 communicates with smart diaper pail 120 and/or mobile device 160 over network 170. Hub 150 can cause an alarm, such as an audible beep or other sound to be emitted, e.g., via a speaker, based on a threshold level of bodily exudate being detected. Hub 150 can also cause a transmission of an alert or a message to another device, for example, operated by a caretaker. Hub 150 can also log events, such as when bodily exudate is detected, to memory for later transmission to a caregiver. Smart diaper pail 120 can maintain a log for later transmission to hub 150. Smart diaper pail 120 can also integrate the functionality of the hub 150 into an on-board computing device located within the smart diaper pail 120.

Mobile device 160 can be any computing device such as a mobile phone, smart phone, tablet, or laptop. Mobile device 160 can perform functions including logging, analysis, and causing alerts. Additionally, or alternatively, mobile device 160 can perform any computational functions of hub 150.

FIG. 2 is a side view of a first example of a smart diaper pail, according to certain aspects of the present disclosure. FIG. 2 depicts smart diaper pail 200, which includes lid 201, weighing chamber 220, analysis chamber 230, and waste chamber 240. Lid 201 can be opened or closed manually (e.g., by a user), or automatically (e.g., by the smart diaper pail itself). When closed, lid 201 can form a seal such that odor from smart diaper pail 200 is minimized.

Weighing chamber 220 includes door 221 and scale 222. Door 221 is positioned between weighing chamber 220 and analysis chamber 230. In an example, a diaper is received by the smart diaper pail 200 and lands in weighing chamber 220, where the diaper's weight is determined by scale 222. Scale 222 can determine a weight of an object in on a metric or other system (e.g., pounds, ounces). At this point, door 221 is in a closed position. Door 221 can be electronically controlled, based on sensors or other signals. For example, door 221 can open or close automatically subsequent to a weight being detected on scale 222.

For example, once the diaper is weighed by scale 222, smart diaper pail 200 can cause door 221 to open and the diaper to fall into analysis chamber 230. Door 221 then closes. Analysis chamber 230 includes light source 231, detector 232, and door 233. Door 233 can be electronically controlled, based on sensors or other signals. Door 233 is initially in a closed position. Light source 231 can stimulate biological structures in the diaper to fluoresce. Light source 231 can emit light at one or more wavelengths.

Detector 232 detects the resulting emitted light from any biological structures. Detector 232 can be any type of light detector such as a photodetector or a camera. Upon completion, smart diaper pail 200 can cause door 233 to open, causing the diaper to fall into waste chamber 240. Smart diaper pail 200 can place or seal the used diaper in a bag and/or can close door 233 to minimize odor escaping.

FIG. 3 is a side view of a first example of a smart diaper pail, according to certain aspects of the present disclosure. FIG. 3 depicts smart diaper pail 300, which includes lid 301, analysis chamber 230, and weighing chamber 320. Lid 301 can be opened or closed manually (e.g., by a user), or automatically (e.g., by the smart diaper pail itself). A diaper is received by the smart diaper pail 300 and lands in analysis chamber 330, where the diaper is analyzed for bodily exudate. Analysis chamber 330 includes light source 331, detector 332, and door 321. At this point, door 321 is in a closed position. Light source 331 can stimulate biological structures in the diaper to fluoresce. Detector 332 detects the resulting emitted light from any biological structures. Detector 332 can be any type of light detector. Smart diaper pail 300 can cause door 321 to open, causing the diaper to fall into weighing chamber 320, where the diaper's weight is determined. Door 321 can open or close automatically. Weighing chamber 320 includes scale 322. For example, once the diaper is weighed by scale 322, smart diaper pail 300 can place or seal the used diaper in a bag. Smart diaper pail 300 can close door 321 to minimize odor escaping.

Figure 4:
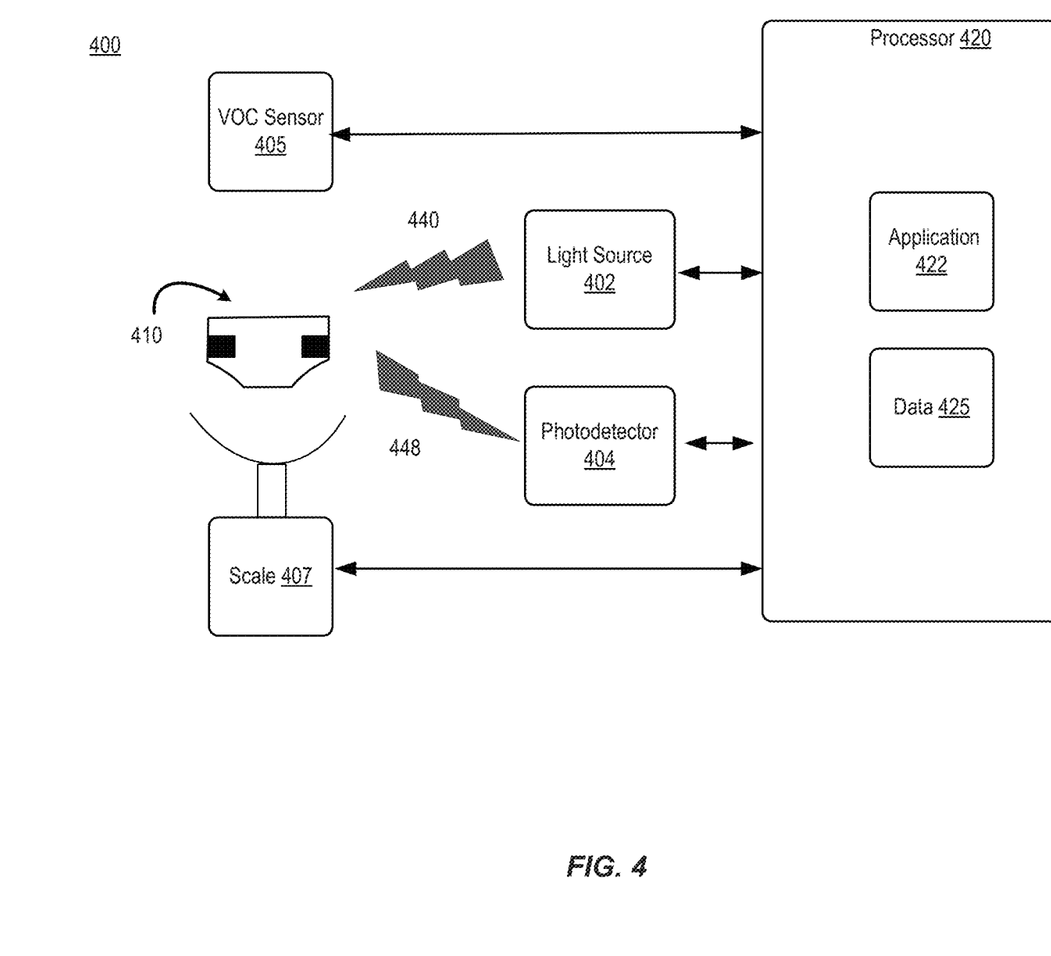
FIG. 4 is a block diagram of a sensing circuit for use in a diaper pail, according to certain aspects of the present disclosure.

FIG. 4 is a block diagram of a sensing circuit for use in a diaper pail, according to certain aspects of the present disclosure. FIG. 4 depicts sensing circuit 400, which includes one or more of light source 402, detector 404, VOC sensor 405, scale 407, article 410, and processor 420. Sensing circuit 400 can detect biological substances, such as bodily exudate, present in article 410. Examples of biological substances include bodily exudate such as feces and urine. Urine can be differentiated from feces based on urine and feces having different fluorescent emission peaks.

Processor 420 can be any processor, signal processor, controller or other processing device. Application 422 can execute on processor 420. Data 425 can include logs, parameters, configuration files, etc., for use by application 422. Processor 420 can control elements of the diaper pail, including door 221, door 233, scale 222, and so forth. Sensing circuit 400 can also include one or more processors, light sources, photodetectors, wireless transmitters, analog-to-digital converters, or digital-to-analog converters (not depicted).

Sensing circuit 400 can detect a presence or an absence of bodily exudate on article 410 by emitting light, causing any bodily exudate (if present) to fluoresce, and measuring returned light, which can include light caused by the fluorescence of bodily exudate (if present) and contributions from other sources. Based on a measurement of the returned light, sensing circuit 400 identifies a presence or absence of substance. Additionally or alternatively, sensing circuit 400 can detect a presence of bodily exudate by using the VOC sensor 405. For example, VOC sensor 405 can detect that VOCs are present and signal to processor 420. Based on the detection, processor 420 can log the particular article as containing bodily exudate. In some cases, processor 420 can use the VOC sensor as a trigger to cause further detection, e.g., via the stimulation and detection of auto-fluorescence.

Light source 402 can emit light at a particular wavelength or range of wavelengths. Examples of light sources include Light Emitting Diodes (LEDs), incandescent lights, and laser diodes. Detector 404 measures light at one or more wavelengths and provides a signal indicative of a strength of the measured light to application 422. Light source 402 can be placed anywhere in the analysis chamber or weighing chamber.

Detector 404 can be any device that can detect and measure light such as a photodetector, photodiode, phototransistor, complementary metal-oxide-semiconductor (CMOS) image sensor, charge-coupled device (CCD) sensor, or photo-resistor. Detector 404 receives light, including light reflected from article 410, whether ambient light or light emitted by light source 402, and generates sensor signals based on that received light. Detector 404 can detect a wide spectrum of light and output information that indicates the detected light. In some cases, detector 404 can provide three outputs e.g., a value that corresponds to red, another value for green, and another value for blue. The values of the triplet correspond to the amplitude of light at a range of wavelengths corresponding to a particular color. Therefore, a first value is proportional to an amplitude of red in the received light, a second value is proportional to an amplitude of green in the received light, and a third value is proportional to an amplitude of blue in the received light. In other cases, such as if detector 404 is a camera, detector 404 receives a matrix or array of pixel values representing the intensity and/or color of pixels. Detector 404 can be placed anywhere in the analysis chamber or weighing chamber.

One or more filters (not shown) can be positioned in front of detector 404. A filter can remove specific range(s) of wavelengths of light to avoid erroneous measurements. For example, a filter that limits transmitted light to the ranges of emission wavelengths of a biological substance can be positioned in front of detector 404. The filter can then remove the excitation light from detection such that the detector does not erroneously detect the light emitted by light source 402.

In some cases, application 422 can perform ambient light compensation by identifying contributions of any spectra of the measured light that is caused by ambient light, e.g., by obtaining a separate measurement of light without light source 402 activated. Even though ambient light can have different color spectra depending on the ambient light source(s) present, application 422 can electronically remove the contribution of such ambient light to light detected by the photodetector and accurately detect light from other sources, such as the light emitted by a fluorescent substance.

In a more specific example, application 422 causes light source 402 to emit light 440. In some cases, a pulse of light is emitted. A pulse can vary temporally, spectrally, and/or spatially. For example, a pulse can be a transmission of light for a specific amount of time, and/or include a specific range of wavelengths of light, and/or include light in one or more directions. In an example, a pulse of light may last for 500 milliseconds. But pulses of different duration can be used. For example, a duration can range from 100 milliseconds to five seconds. In turn, light 440 causes bodily exudate, if present in article 410, to fluoresce. Application 422 receives, from detector 404, an intensity of returned light. Any contributions of ambient light are removed from the measurement of returned light 448. The amount of returned light 448 at one or more particular wavelengths then indicates a presence and amount of bodily exudate. The intensity of returned light 448 can be compared to a light intensity threshold.

If the detected intensity is greater than a light intensity threshold, then application 422 determines that bodily exudate is present. Otherwise, application 422 determines that bodily exudate is absent. Upon the detection, application 422 can perform one or more actions. For example, application 422 can transmit a notification to hub 150, cause an audible or visual alert, or create a log of the presence or absence of bodily exudate. An example of a process performed by application 422 to detect a presence or absence of a substance is discussed further with respect to FIG. 5.

A given fluorophore has a spectra of light at which it will absorb energy (some of which can be emitted) and a spectra that is emitted when it fluoresces and therefore may be characterized by an excitation curve and an emission curve. An excitation curve specific to a particular wavelength represents an amount of light emitted at the particular wavelength for a range of excitation wavelengths. For example, a particular chemical may emit light when excited by incoming light with a peak wavelength substantially at 600 or 650 nm, where the light emitted when excited at the peak wavelength of 600 nm is greater in intensity than the light emitted when excited at 650 nm. Therefore, the substance is said to absorb more energy at 600 nm than at 650 nm. An absorption curve for a given fluorophore represents the amount of energy that is absorbed for the particular wavelength. The absorption and excitation spectra are distinct, but often overlap.

An emission curve represents a range of wavelengths of light that are emitted for a given excitation wavelength. For example, an excitation curve for a chemical when stimulated with light with a peak wavelength of 420 nm may output a peak intensity at 630 nm and lower intensity light at other wavelengths. Typically, the most efficient excitation wavelength is close to the maximum peak of the absorption spectra. The difference between the peak excitation wavelength and the peak emission wavelength is called the Stokes' shift.

Sensing circuit 400 can adjust the wavelength(s) of emitted light to maximize a response of the substance to be detected and to minimize fluorescence of the article or any other substances. For example, an excitation wavelength with a lower absorption can sometimes result in a lower total intensity of emission, but there is not necessarily a direct linear correlation. This property can be leveraged to minimize background fluorescence by choosing an excitation spectra that includes peaks representing wavelengths that are poorly absorbed by any background material, including any undesired fluorophores, and high for the substance of interest. Alternatively, a ratio-based approach of sensing can be performed by using multiple excitation wavelengths and measuring the difference in response.

In an example, light with one or more peak wavelengths is provided to an article. In turn, light emitted at one or more ranges of emission wavelengths can be detected. For example, sensing circuit 400 can excite a substance by providing light that includes two different peak wavelengths, each of which corresponds to an excitation wavelength of a biological substance that is to be detected. In an example, light with a first peak excitation wavelength is first emitted, followed by a first measurement of the response, then light that includes a second peak excitation wavelength is emitted, followed by a second measurement of a subsequent response. By analyzing an intensity of the measurements and/or a ratio of the measurements, disclosed solutions can detect a presence of a biological substance. Any number of excitation wavelengths and/or emission wavelengths can be used. The peak wavelengths can be identical or different. The peak wavelengths can overlap or not overlap, e.g., be mutually exclusive. Different combinations are possible.

Figure 5:
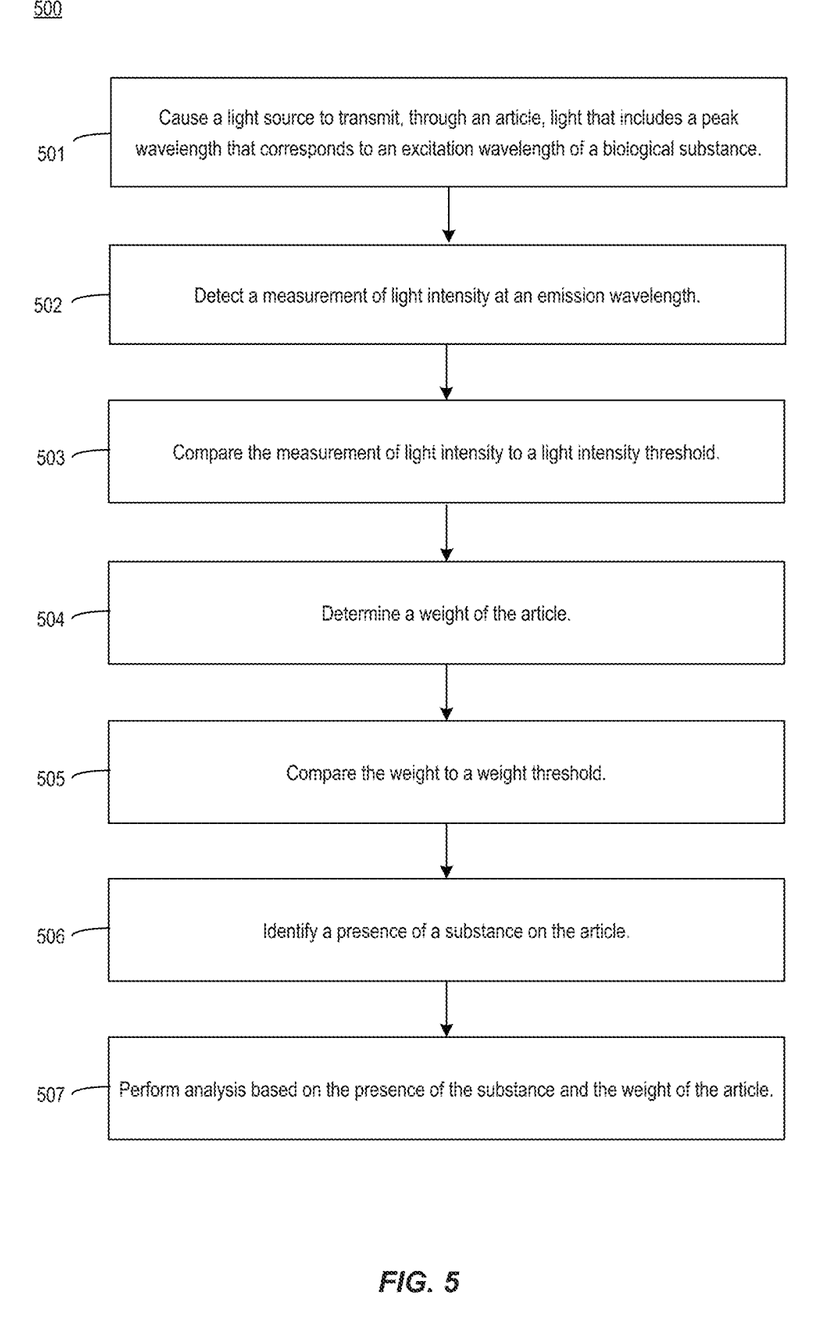
FIG. 5 is a flowchart depicting an example of a process used to analyze an absorbent article, according to certain aspects of the present disclosure.

FIG. 5 is a flowchart depicting an example of a process used to analyze an absorbent article, according to certain aspects of the present disclosure. Process 500 can be implemented by sensing circuit 400 (e.g., software executing on processor 420) or another system. With respect to autofluorescence, process 500 describes a simplified example using one excitation wavelength and one emission wavelength, but other configurations are possible. Further, process 500 describes weighing being performed subsequent to substance detection, but weighing can alternatively be performed prior to or during substance detection.

At block 501, process 500 involves causing a light source to transmit, through an article, light that includes a peak wavelength that corresponds to an excitation wavelength of a biological substance. The peak wavelength can be selected based on the substance to be detected.

Biological substances can include bodily exudate. Bodily exudate can include fluorophores. For example, chlorophyll, secreted as a result of digesting vegetables can be present in bodily exudate and therefore can be tested. But for some human subjects, for example, babies, the detection of chlorophyll as a proxy for detecting a bowel movement can lead to false negatives because young infants do not eat solid foods. In contrast, porphyrins, which are also present in bowel movements as a byproduct of the body making hemoglobin, are a more reliable indicator that can be detected. Humans that are more efficient at manufacturing hemoglobin may emit lower quantities of porphyrins, but porphyrins are nevertheless still present in bodily exudate. Porphyrins have a high emission at specific wavelengths. Man-made structures, such as diapers, can also fluoresce, as well as other naturally occurring substances such as skin. Accordingly, contributions from other sources of fluorescence can be separated from a measurement of bodily exudate. In the case that chlorophyll and porphyrins are both present, the presence can be disambiguated due to the different response curves.

Figure 6:
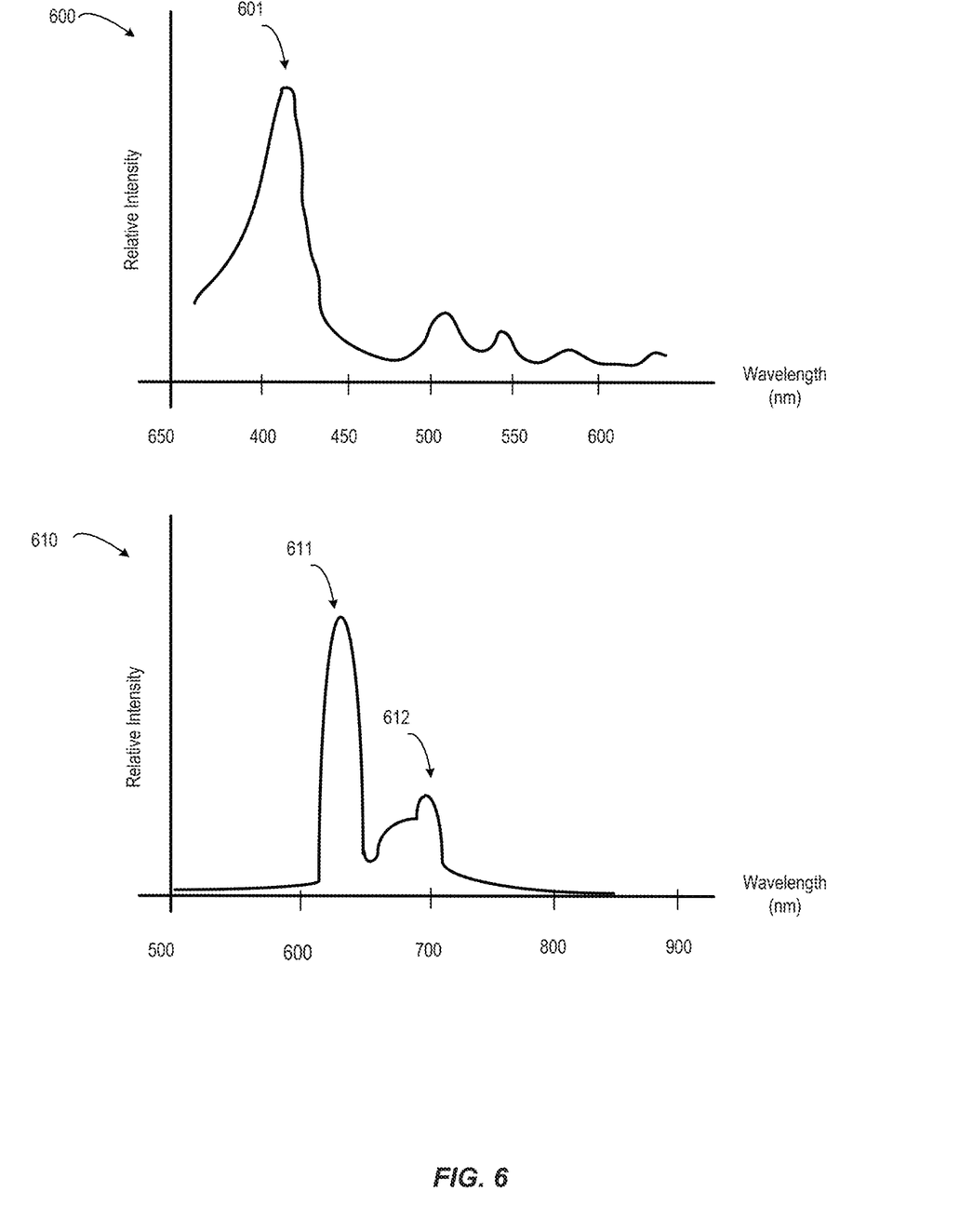
FIG. 6 depicts excitation and emission curves for a biological substance.

FIG. 6 depicts excitation and emission curves for a biological substance. As depicted in the example of FIG. 6, the substance has an excitation curve as shown in graph 600 and an emission curve as shown in graph 610. The x-axis represents wavelengths of light and the y-axis represents a relative intensity. As depicted, the substance can be excited in various spectral regions ranging from violet light (405 nm) to near-infrared (around 700 nm). In particular, the excitation curve has peak 601 around 460 nm, which represents a wavelength at which a greater amount of energy is absorbed given a light source of equal amplitude relative to other wavelengths. The x-axis represents wavelengths of light and the y-axis represents a relative intensity. As depicted, the emission curve includes a peak 611 around 660 nm and second, smaller peak 612 around 700 nm.

Returning to FIG. 5, at block 502, process 500 involves detecting a measurement of light intensity at an emission wavelength (or a range of emission wavelengths). Continuing the example, application 422 detects returned light at 700 nm.

At block 503, process 500 involves comparing the measurement of light intensity to a light intensity threshold. For example, sensing circuit 400 compares the amount of returned light at 630 nm to a light intensity threshold. A measurement of light intensity that is greater than the intensity threshold can indicate that bodily exudate is present on or in the article.

At block 504, process 500 involves determining a weight of the article. For example, sensing circuit 400 obtains a weight from scale 407. In certain cases, the weight can directly indicate a weight of the diaper. In other cases, the weight can be a total weight of all diapers in the pail (for example, as depicted in FIG. 3). In this manner, sensing circuit 400 can obtain a weight before a diaper is placed in weighing chamber 320 and afterwards (e.g., after door 321 opens). In this case, the weight of the last diaper placed in the chamber equals the difference of the weight after and the weight before. The weight of the bodily exudate itself can be determined by subtracting a known empty weight of a diaper from the measured weight.

At block 505, process 500 involves comparing the weight to a weight threshold. For example, processor 420 can determine the average weight of a bowel movement across multiple diapers. For each diaper received, processor 420 can determine whether a bowel movement is present. If so, then processor 420 causes scale 407 to weigh the diaper and subtract a known empty diaper weight from the diaper. The weight of the diaper is added to a running sum to determine the average bowel movement weight. In a similar fashion, processor 420 can determine the average weight of urine for a set of diapers. For each diaper received, processor 420 can determine whether a urine is present. If so, then processor 420 can cause scale 407 to weigh the diaper and subtract a known empty diaper weight from the diaper. The weight of the diaper is added to a running sum to determine the average urine weight.

At block 506, process 500 involves identifying a presence of a substance on the article. The presence or absence of a biological substance can be determined by the light intensity being greater than a threshold, the weight being greater than a weight threshold, or both. An absence of the substance can be determined when the light intensity is less than the light intensity threshold, the weight is less than the weight threshold, or both.

For example, if the determined weight is greater than a weight threshold, then sensing circuit 400 determines that a substance is within or absorbed by the article. In another example, sensing circuit 400 can identify a presence of a substance on the article based on the returned light being higher than a light intensity threshold. If the amount of returned light is less than the light intensity threshold, then sensing circuit 400 can identify an absence of the substance.

In another example, a sensing circuit first determines whether the weight is greater than the weight threshold, then if so, continues to determine whether the light intensity is greater than the light intensity threshold. Based on both the weight threshold and the light intensity threshold being met, a presence of a substance is identified.

Therefore, blocks 502-503 and blocks 504-505 can operate independently or in conjunction with each other. In some cases, blocks 502-503 are performed and blocks 504-505 are not performed. In other cases, blocks 504-505 are performed and blocks 502-503 are not performed. The presence or absence of the substance can be transmitted to hub 150 or another device.

At block 507, process 500 involves performing analysis based on the presence of the substance and the weight of the article. Processor 420 can create logs. A log can include multiple entries, for example, date, time, bowel movement size or amount, urine size or amount, type of diaper, etc. Based on the log, processor 420 can determine trends. For example, processor 420 can determine a frequency of bowel movement (e.g., every two hours, or every five hours). Then, processor 420 can determine whether the infant is having more bowel movements than usual.

Processor 420 can determine regularity of a bowel movement. Regularity can be identified as a frequency (e.g., once per day). Processor 420 can then determine and note any deviations from the determined regularity. For example, processor 420 can determine whether a weight of an average bowel movement or an average volume of urine can be noted and analyzed for trends (increases or decreases). Trends could be sudden or gradual. These changes, or other changes, e.g., a change in an average intensity of fluorescence of bodily exudate or VOCs for a given weight can indicate that the health of an individual has changed. In some cases, different and/or multiple excitations and/or emission wavelengths can be used. By carefully selecting the appropriate ranges of wavelengths of emitted light, any auto-fluorescence from a diaper can be minimized, while auto-fluorescence from bodily exudate maximized. Further, a diaper can absorb light and can absorb different amounts of light at different wavelengths. Consequently, an amount of light that reaches the bodily exudate can be reduced, resulting in lower, or almost zero fluorescence. In these cases, a measure of emitted light after stimulation can be considered a reference measurement of the fluorescence of another object, e.g., a diaper. In some aspects, longer wavelengths, which can penetrate a diaper better, can be included in the ranges of wavelengths that are emitted. In yet further aspects, a large range or sweep of excitation wavelengths (e.g., from 400 to 700 nm) can be used.

For example, a multiple-excitation and single emission approach can be used. As further discussed, a multiple-excitation, single-emission approach is one of many approaches utilized by disclosed systems. With the multiple-excitation, single-emission approach, application 422 identifies a first amount of light emitted at a specific range of wavelengths when the substance is stimulated by light that includes a first excitation wavelength. Application 422 further identifies a second amount of light emitted at a second specific range of wavelengths when the substance is stimulated by light including a second peak wavelength.

Application 422 causes a light source to transmit, through an article, light that includes a first peak wavelength that corresponds to a first excitation wavelength of a biological substance. For example, application 422 can cause light source 402 to transmit light at 430 nm. As can be seen in FIG. 6, 430 nm corresponds to peak 601 on graph 600. Accordingly, causing light to be emitted at 430 nm can stimulate the substance to fluoresce. However, in some cases, light at 430 nm may not pass through the article, meaning that any substance therein will not be excited. Therefore, any measured light caused in response to the 430 nm excitation may solely be due to fluorescence of the article itself. In this case, therefore, the returned light represents a measure of the fluorescence of the article, which can be used as a baseline measurement.

Application 422 obtains a first measurement of light intensity within a range of emission wavelengths. Application 422 receives, from detector 404, a first measure of light at 600 nm. Application 422 can wait for a small time (e.g., on the order of nanoseconds) for residual fluorescent effects to diminish.

Application 422 causes a second light source to transmit, through an article, light that includes a second peak wavelength that corresponds to a second excitation wavelength of the biological substance. Application 422 causes light source 402 to transmit light at 510 nm, which is expected to be absorbed by the substance (see graph 600).

Application 422 detects, at the photodetector, a second measurement of light intensity at a second emission wavelength. Application 422 receives, from detector 404, a second measure of light at 600 nm. Application 422 identifies a presence of a substance on the article by comparing a ratio between the first measurement of light intensity and the second measurement of light intensity against a light intensity threshold. Application 422 computes a ratio of the first measure to the second measure.

By using multiple wavelengths and deriving ratios of amplitudes of light at the different wavelengths relative to a baseline, sensing circuit 400 can disambiguate contributions in returned light measured at detector 404 caused by bodily exudate from contributions that are caused by other substances. For example, application 422 can compare a ratio of light intensity emitted at 700 nm when the bodily exudate is excited at 610 nm to a measure of light intensity at 700 nm when the substance is excited at 430 nm, with a predefined, or calibrated ratio established as a baseline when no bodily exudate is known to be present.

Additionally, if detector 404 is a camera, sensing circuit 400 can identify changes in a ratio across the entire diaper area. For instance, an area of the diaper with no bodily exudate might have a low ratio, whereas an area with bodily exudate might have a higher ratio. This determination, for example, if the ratio is relatively constant across a detected image, then no bodily exudate is present. Alternatively, the ratio can be used to identify a volume of exudate present based on the ratio that is higher. For example, if the ratio is higher in a first area versus in a second area, then sensing circuit 400 identifies that a first volume of bodily exudate present is present in the first area. In other cases, the ratio measured in a particular location of the absorbent article is compared to one or more thresholds. Each threshold can indicate a specific volume of bodily exudate present.

Further, a ratio can help detect substances within a diaper that is non-uniform in shape or non-uniform in distance from the detector. For example, a diaper can be more swollen in one area than in another area or bundled more tightly in one area than another. A diaper placed in the analysis chamber can land anywhere in the chamber, at any angle with respect to the detector. For example, while the intensity changes, the ratio between the two emission wavelengths remains similar, thereby enabling the detection of the auto-fluorescence of the bodily exudate. Returning to the example, application 422 determines a ratio of light emitted at 700 nm when excited at 610 nm to light emitted at 600-700 nm when excited at 430 nm of 5:1. Application 422 compares the ratio to a baseline ratio, when no bodily exudate is present, of 1:1. Based on the detected ratio being greater, the application 422 determines that the bodily exudate is present.

Figure 7:
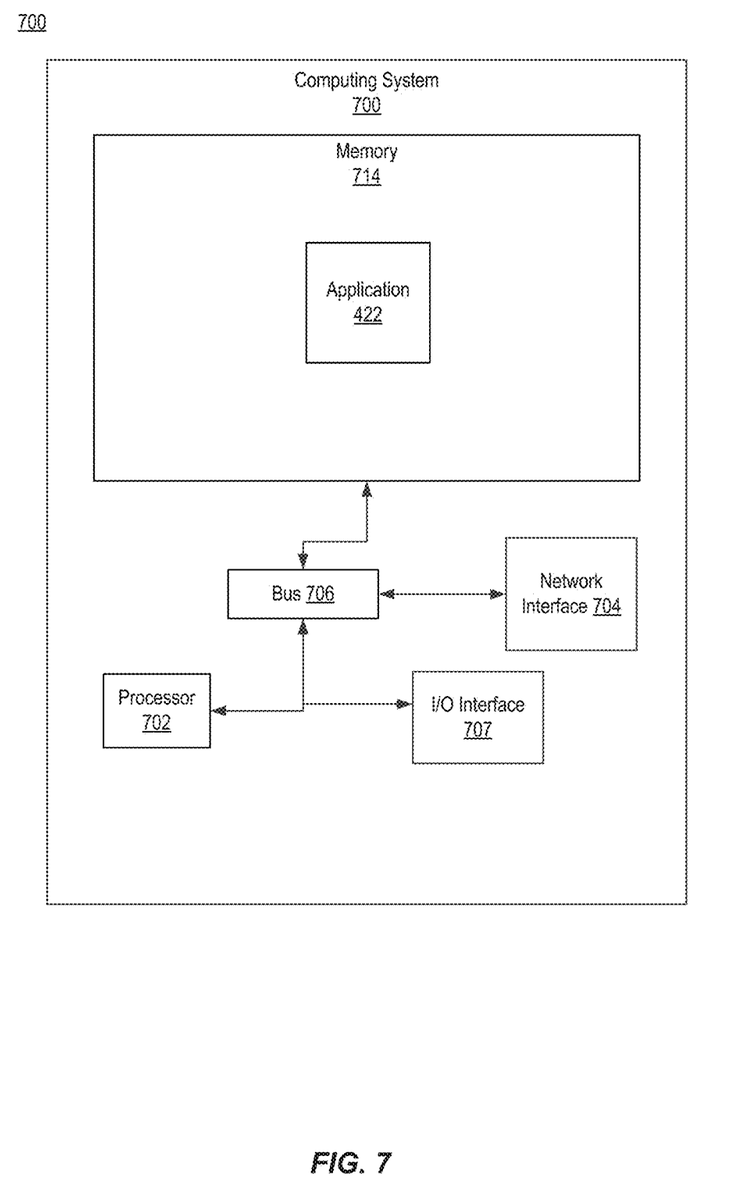
FIG. 7 is a diagram depicting an example computing system for performing functions related to analyzing diapers within a diaper pail, according to some aspects of the present disclosure.

FIG. 7 is a diagram depicting an example computing system for performing functions related to analyzing diapers within a diaper pail, according to some aspects of the present disclosure.

Some or all of the components of the computing system 700 can belong to processor 420 of FIG. 4. For example, the application 422 may operate on the computing system 700. The computing system 700 includes one or more processors 702 communicatively coupled to one or more memory devices 714. The processor 702 executes computer-executable program code, which can be in the form of non-transitory computer-executable instructions stored in the memory device 714, accesses information stored in the memory device 714, or both. Examples of the processor 702 include a microprocessor, an application-specific integrated circuit ("ASIC"), a field-programmable gate array ("FPGA"), or any other suitable processing device. The processor 702 can include any number of processing devices, including one.

The memory device 714 includes any suitable computer-readable medium such as electronic, optical, magnetic, or other storage device capable of providing a processor with computer-readable instructions or other program code. Non-limiting examples of a computer-readable medium include a magnetic disk, a memory chip, a ROM, a RAM, an ASIC, optical storage, magnetic tape or other magnetic storage, or any other medium from which a processing device can read instructions. The instructions may include processor-specific instructions generated by a compiler or an interpreter from code written in any suitable computer-programming language, including, for example, C, C++, C#, Visual Basic, Java, Python, Perl, JavaScript, and ActionScript.

The computing system 700 may also include a number of external or internal devices such as input or output devices. For example, the computing system 700 is shown with an input/output ("I/O") interface 707 that can receive input from input devices or provide output to output devices. A bus 706 can also be included in the computing system 700. The bus 706 can communicatively couple one or more components of the computing system 700 and allow for communication between such components.

The computing system 700 executes program code that configures the processor 702 to perform one or more of the operations described above, for example as described with respect to FIG. 5. The program code of the application 422, which can be in the form of non-transitory computer-executable instructions, can be resident in the memory device 714 or any suitable computer-readable medium and can be executed by the processor 702 or any other one or more suitable processor. Execution of such program code configures or causes the processor(s) to perform the operations described herein. In additional or alternative aspects, the program code described above can be stored in one or more memory devices accessible by the computing system 700 from a remote storage device via a data network. The processor 702 can use the memory device 714. The memory device 714 can store, for example, additional programs, or data used by the applications executing on the processor 702 such as the application 422.

The computing system 700 can also include at least one network interface 704. The network interface 704 includes any device or group of devices suitable for establishing a wired or wireless data connection to one or more data networks. Non-limiting examples of the network interface 704 include an Ethernet network adapter, WiFi network, Bluetooth, or Bluetooth Low Energy (BLE), a modem, or the like. The computing system 700 is able to communicate with one or more other computing devices or computer-readable data sources via a data network using the network interface 704.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multi-purpose microprocessor-based computer systems accessing stored software that programs or configures the computing system from a general purpose computing apparatus to a specialized computing apparatus implementing one or more aspects of the present subject matter. Any suitable programming, scripting, or other type of language or combinations of languages may be used to implement the teachings contained herein in software to be used in programming or configuring a computing device.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

That which is claimed is:

1. A diaper pail comprising:
a first chamber, a second chamber, and a door between the first chamber and second chamber, wherein the first chamber and the second chamber are vertically stacked and connected by the door, wherein the first chamber comprises a scale, wherein the second chamber comprises a light source, a photodetector, and a processor,
wherein the scale is configured to determine a weight of an absorbent article, the absorbent article comprising sides;
wherein the light source is positioned to transmit light directed at one or more sides of the absorbent article, wherein the light includes a peak excitation wavelength that corresponds to an excitation wavelength of a biological substance such that the light increases autofluorescence emission within a range of emission wavelengths and reduces autofluorescence emission of other substances or the absorbent article;
wherein the photodetector is configured to detect light intensity within the range of emission wavelengths of the biological substance and to output a measurement of the light intensity, wherein the photodetector is positioned to detect light emitted from the one or more sides of the absorbent article; and
wherein the processor is configured to execute processor-executable instructions to cause the processor to:
receive, from the scale, the weight of the absorbent article;
receive, from the photodetector, the measurement of the light intensity;
compare the measurement of light intensity to a light intensity threshold or determine that the weight of the absorbent article is greater than a weight threshold;
determine a presence of the biological substance on the absorbent article based on the comparing or determining; and
transmit a message indicating the presence of the biological substance to an external device.

2. The diaper pail of claim 1, wherein the excitation wavelength is between 405 and 550 nm.

3. The diaper pail of claim 1, wherein the processor is further configured to execute processor-executable instructions to:
obtain a baseline measurement of light intensity comprising a contribution of ambient light; and
remove the baseline measurement of light intensity from the measurement of light intensity.

4. The diaper pail of claim 1, wherein the peak excitation wavelength is between 405 and 650 nm and the range of emission wavelengths is either 620 to 640 nm or 650 to 710 nm.

5. The diaper pail of claim 1, wherein the biological substance is a porphyrin.

6. The diaper pail of claim 1, further comprising a volatile organic compound sensor positioned to detect a level of volatile organic compound present in the absorbent article and provide the level of volatile organic compound to the processor, wherein the processor is further configured to execute processor-executable instructions to:
receive, from the volatile organic compound sensor, the level of volatile organic compound,
compare the level of volatile organic compound to an additional threshold, and
wherein determining the presence of the biological substance on the absorbent article is further based on comparing the level of volatile organic compound to the additional threshold.

7. The diaper pail of claim 1,
wherein the first chamber further comprises a sensor positioned to detect a presence of the absorbent article in the first chamber, and wherein the processor is further configured to execute processor-executable instructions to cause the processor to:
receive, from the sensor, an indication that the absorbent article is present in the first chamber, and
responsive to obtaining the weight from the scale, cause the door to open.

8. The diaper pail of claim 7, further comprising a third chamber adjacent to the second chamber, wherein the second chamber comprises an additional door, and wherein the processor is further configured to execute processor-executable instructions to cause the additional door to open, thereby causing the absorbent article to fall into the third chamber.

9. The diaper pail of claim 1, wherein the peak excitation wavelength corresponds to a low absorption wavelength for the other substances and the absorbent article.

10. A method comprising:
detecting, by a processor, a presence of an absorbent article in a first chamber of a diaper pail, wherein the diaper pail comprises the first chamber, a second chamber, and a door between the first chamber and second chamber, wherein the first chamber and the second chamber are vertically stacked and connected by the door, wherein the first chamber comprises a scale, wherein the second chamber comprises a light source, a photodetector, and the processor;
obtaining, by the processor from the scale, a weight of the absorbent article;
causing, at a first time by the processor, the light source to transmit light at one or more sides of the absorbent article, wherein the light includes a peak excitation wavelength that corresponds to an excitation wavelength of a biological substance such that the light increases autofluorescence emission of the biological substance within a range of emission wavelengths and reduces autofluorescence emission of other substances or the absorbent article;
receiving, by the processor from a photodetector, a first measurement of light intensity within a first range of emission wavelengths of the biological substance;
responsive to comparing the first measurement of light intensity to a light intensity threshold and determining that the weight of the absorbent article is greater than a weight threshold, identifying, by the processor, a presence of the biological substance on the absorbent article; and
transmitting, by the processor, a message indicating the presence of the biological substance to an external device.

11. The method of claim 10, further comprising receiving, from a volatile organic compound sensor, a level of volatile organic compound, wherein identifying the presence of the biological substance further includes comparing the level of volatile organic compound to an additional threshold.

12. The method of claim 10, further comprising:
    obtaining, from the photodetector, a baseline measurement of light intensity comprising a contribution of ambient light; and
    removing, the baseline measurement of light intensity from the first measurement of light intensity.

13. The method of claim 10, wherein causing the light source to transmit light occurs in response to determining that the weight of the absorbent article is greater than the weight threshold.

\* \* \* \* \*